United States Patent
Allio et al.

(10) Patent No.: US 10,449,165 B2
(45) Date of Patent: Oct. 22, 2019

(54) FOODS, SYSTEMS, METHODS, AND KITS FOR PROVIDING ELECTROLYTE REPLACEMENT

(71) Applicant: ColonaryConcepts LLC, Newton, MA (US)

(72) Inventors: Michael Allio, Providence, RI (US); Jonathan Gordon, Providence, RI (US)

(73) Assignee: COLONARYCONCEPTS LLC, Newton, MA (US)

( * ) Notice: Subject to any disclaimer, the term of this patent is extended or adjusted under 35 U.S.C. 154(b) by 0 days.

(21) Appl. No.: 15/611,390

(22) Filed: Jun. 1, 2017

(65) Prior Publication Data

US 2017/0266129 A1    Sep. 21, 2017

Related U.S. Application Data

(62) Division of application No. 14/699,973, filed on Apr. 29, 2015, now Pat. No. 9,693,972.

(60) Provisional application No. 62/141,758, filed on Apr. 1, 2015, provisional application No. 61/986,048, filed on Apr. 29, 2014.

(51) Int. Cl.

| | |
|---|---|
| *A61K 31/08* | (2006.01) |
| *A61K 33/14* | (2006.01) |
| *A61K 33/00* | (2006.01) |
| *A61K 45/06* | (2006.01) |
| *A23L 33/10* | (2016.01) |
| *A23L 33/16* | (2016.01) |
| *A23L 29/288* | (2016.01) |
| *A23L 7/126* | (2016.01) |
| *A23L 7/13* | (2016.01) |
| *A23L 13/40* | (2016.01) |
| *A23L 17/00* | (2016.01) |
| *A61K 31/77* | (2006.01) |

(52) U.S. Cl.
CPC .............. *A61K 31/08* (2013.01); *A23L 7/126* (2016.08); *A23L 7/13* (2016.08); *A23L 13/40* (2016.08); *A23L 13/42* (2016.08); *A23L 13/432* (2016.08); *A23L 17/00* (2016.08); *A23L 29/288* (2016.08); *A23L 33/10* (2016.08); *A23L 33/16* (2016.08); *A61K 31/77* (2013.01); *A61K 33/00* (2013.01); *A61K 33/14* (2013.01); *A61K 45/06* (2013.01); *A23V 2002/00* (2013.01)

(58) Field of Classification Search
CPC ........ A61K 31/08; A61K 45/06; A61K 33/00; A61K 33/14; A23L 1/30; A23L 1/304; A23V 2002/00
See application file for complete search history.

(56) References Cited

U.S. PATENT DOCUMENTS

| | | | |
|---|---|---|---|
| 2,367,166 A | | 1/1945 | Balston |
| 4,476,121 A | | 10/1984 | Moss |
| 4,871,557 A | | 10/1989 | Linscott |
| 5,232,699 A | * | 8/1993 | Colliopoulos ....... A61K 36/185 424/727 |
| 5,258,181 A | * | 11/1993 | Cregier .................. A23G 3/346 424/738 |
| 5,323,699 A | | 6/1994 | Motoe et al. |
| 5,612,074 A | | 3/1997 | Leach |
| 5,710,183 A | | 1/1998 | Halow |
| 6,048,901 A | | 4/2000 | Cleveland et al. |
| 6,162,464 A | | 12/2000 | Jacob et al. |
| 6,444,198 B1 | | 9/2002 | Daggy et al. |
| 6,447,763 B1 | | 9/2002 | Gordon |
| 6,576,253 B2 | | 6/2003 | Schramm et al. |
| 6,645,481 B1 | | 11/2003 | Cleveland et al. |
| 6,866,873 B2 | | 3/2005 | Stern |
| 6,939,563 B2 | | 9/2005 | Corpet et al. |
| 6,946,149 B2 | | 9/2005 | Cleveland |
| 7,169,381 B2 | | 1/2007 | Barras et al. |
| 7,256,202 B2 | | 8/2007 | Halow |

(Continued)

FOREIGN PATENT DOCUMENTS

| | | |
|---|---|---|
| CA | 2424587 A1 | 4/2002 |
| CN | 101897721 A | 12/2010 |

(Continued)

OTHER PUBLICATIONS

Altinbas et al., Adding pineapple juice to a polyethylene glycol-based bowel cleansing regime improved the quality of colon cleaning. Annuals of Nutrition and Metabolism: European Journal of Nutrition, Metabolic Diseases and Diet. 63(No. 1-2)83-87, 2013.

(Continued)

*Primary Examiner* — Sudhakar Katakam (74) *Attorney, Agent, or Firm* — Wilson Sonsini Goodrich & Rosati (57) ABSTRACT

Described herein are methods, compositions, systems, and kits that effectively deliver a laxative to a patient along with effective electrolyte replenishment by delivering both a laxative and electrolytes via a food item. The food item is prepared by either combining, mixing, or integrating the ingredients that form the food item together with one of or both of a laxative and electrolytes so that the ingredients in the food item either eliminate or significantly reduce the poor taste associated with either the electrolytes or the laxative. Eliminating or reducing the poor taste associated with either electrolytes or laxative, greatly improves patient satisfaction and compliance with ingesting these substances in order to, for example, prepare the GI tract of the patient for a medical or surgical procedure.

25 Claims, 2 Drawing Sheets

(56) References Cited

U.S. PATENT DOCUMENTS

| | | |
|---|---|---|
| 7,282,223 B2 | 10/2007 | Stern |
| 7,291,324 B2 | 11/2007 | Pelham et al. |
| 7,332,184 B2 | 2/2008 | Vanner et al. |
| 7,495,063 B2 | 2/2009 | Thompson et al. |
| 7,658,914 B2 | 2/2010 | Barras et al. |
| 7,718,197 B2 | 5/2010 | Skiendzielewski et al. |
| 7,955,632 B2 | 6/2011 | Paulsen et al. |
| 8,057,831 B2 | 11/2011 | Donaldson |
| 8,114,455 B2 | 2/2012 | Paulsen et al. |
| 8,211,417 B1 | 7/2012 | Snady |
| 8,247,008 B2 | 8/2012 | Donaldson |
| 8,361,452 B2 | 1/2013 | Halow |
| 8,425,944 B2 | 4/2013 | Caswell |
| 8,507,009 B2 | 8/2013 | Skiendzielewski et al. |
| 8,778,306 B2 | 7/2014 | Bachwich |
| 8,829,017 B2 | 9/2014 | Forbes et al. |
| 9,655,919 B2 | 5/2017 | Korzenik et al. |
| 9,693,972 B2 | 7/2017 | Allio et al. |
| 2004/0009236 A1 | 1/2004 | Halow |
| 2005/0152989 A1 | 7/2005 | Pelham et al. |
| 2006/0029570 A1 | 2/2006 | Aronson et al. |
| 2007/0166411 A1 | 7/2007 | Anthony et al. |
| 2008/0213393 A1 | 9/2008 | Skiendzielewski et al. |
| 2008/0260682 A1 | 10/2008 | Rose et al. |
| 2009/0053304 A1* | 2/2009 | Chen ............... A61K 9/5026 424/451 |
| 2009/0324736 A1 | 12/2009 | Johnson et al. |
| 2010/0010101 A1 | 1/2010 | Cherukuri |
| 2010/0159026 A1 | 6/2010 | Skiendzielewski et al. |
| 2010/0178360 A1 | 7/2010 | Deviere et al. |
| 2010/0255122 A1* | 10/2010 | Garren ............... A61K 9/0095 424/679 |
| 2010/0278949 A1 | 11/2010 | Scott |
| 2011/0065740 A1 | 3/2011 | Forbes et al. |
| 2011/0223252 A1 | 9/2011 | Borody et al. |
| 2011/0288180 A1 | 11/2011 | Korzenik et al. |
| 2012/0021064 A1 | 1/2012 | Patton |
| 2012/0107430 A1 | 5/2012 | Scott |
| 2013/0164384 A1 | 6/2013 | Johnson et al. |
| 2013/0189377 A1 | 7/2013 | Cockett et al. |
| 2013/0225692 A1 | 8/2013 | Stein et al. |
| 2014/0080906 A1 | 3/2014 | Ervin et al. |
| 2014/0235730 A1 | 8/2014 | Subramanian et al. |
| 2014/0255495 A1 | 9/2014 | Bachwich |
| 2015/0224127 A1 | 8/2015 | Nizam |
| 2015/0306046 A1 | 10/2015 | Allio et al. |
| 2016/0206650 A1 | 7/2016 | Korzenik et al. |

FOREIGN PATENT DOCUMENTS

| | | |
|---|---|---|
| CN | 102805752 A | 12/2012 |
| DE | 102006001199 A1 | 7/2007 |
| EP | 0423771 A2 | 4/1991 |
| EP | 0423771 B1 | 6/1994 |
| EP | 1326592 A1 | 7/2003 |
| EP | 1337264 A1 | 8/2003 |
| EP | 2709641 A1 | 3/2014 |
| EP | 3137167 A1 | 3/2017 |
| JP | 2007217398 A | 8/2007 |
| NZ | 525533 A | 9/2004 |
| WO | WO-0226222 A2 | 4/2002 |
| WO | WO-0230439 A1 | 4/2002 |
| WO | WO-03086172 A2 | 10/2003 |
| WO | WO-2004006833 A2 | 1/2004 |
| WO | WO-2006069422 A1 | 7/2006 |
| WO | WO-2006122104 A1 | 11/2006 |
| WO | WO-2007083594 A1 | 7/2007 |
| WO | WO-2010006209 A3 | 4/2010 |
| WO | WO-2010081781 A1 | 7/2010 |
| WO | WO-2012158048 A1 | 11/2012 |
| WO | WO-2013044085 A1 | 3/2013 |
| WO | WO-2014032108 A1 | 3/2014 |
| WO | WO-2015168330 A1 | 11/2015 |
| WO | WO-2017040860 A1 | 3/2017 |

OTHER PUBLICATIONS

European Patent Application No. 15788236.9 extended European Search Report dated Nov. 21, 2017.
Canadian Patent Application No. 2,736,183 Further Examiner's Report dated Jan. 30, 2017.
Canadian Patent Application No. 2,736,183 Office Action dated Mar. 17, 2016.
Canadian Patent Application No. 2,736,183 Office Action dated May 21, 2015.
Dahshan et al., A randomized, prospective study to evaluate the efficacy and acceptance of three bowel preparations for colonoscopy in children. Am. J. Gastroenterol, 94(12):3497-3501 (1999).
Database WPI, Week 200841, Thomson Scientific, London, GB; AN 2008-G53654 (Jul. 26, 2007).
Delegge and Kaplan, Efficacy of bowel preparation with the use of a prepackaged, low fiber diet with a low sodium, magnesium citrate cathartic vs. a clear liquid diet with a standard sodium phosphate cathartic. Aliment Pharmacol. Therapy, 21:1491-1495, 2005.
European Patent Application No. 09795214 Office Action dated Sep. 26, 2016.
European Patent Application No. 09795214 Communication dated Aug. 6, 2015.
European Patent Application No. 09795214 Supplementary European Search Report dated Nov. 24, 2011.
Hawes et al., A consensus document on bowel preparation before colonoscopy: prepared by a task force from the American Society of Colon and Rectal Surgeons (ASCRS), the American Society for Gastrointestinal Endoscopy (ASGE), and the Society of American Gastrointestinal and Endoscopic Surgeons (SAGES), Gastrointentinal Endoscopy, 63(7):894-909 (2006).
Japanese Patent Application No. 11-343251, published Dec. 14, 1999.
Nutrition Facts for Plums, Dried (Prunes), uncooked (accessed online at http://nutritiondata.self.com/facts/fruits-and-fruit-juices/2043/2, Aug. 1, 2016), 4 pages.
PCT Patent Application No. PCT/US2009/050167 International Search report and Written Opinion dated Feb. 9, 2010.
PCT Patent Application No. PCT/US2015/028361 International Search Report and Written Opinion dated Jul. 23, 2015.
PCT/US2015/028361 International Preliminary Report on Patentability dated Nov. 10, 2016.
Siegel et al., Medical Treatment of Constipation. Clinics in Colon and Rectal Surgery, 18:76-80, 2005.
U.S. Appl. No. 14/699,973 Office Action dated Jan. 14, 2016.
U.S. Appl. No. 14/699,973 Office Action dated Jul. 5, 2016.
U.S. Appl. No. 15/085,363 Office Action dated Aug. 10, 2016.
U.S. Appl. No. 15/085,363 Office Action dated Dec. 13, 2016.
Eurasian Patent Application No. 201692106 Office Action dated May 4, 2018.
European Patent Application No. 09795214.7 Communication pursuant to Article 94(3) EPC dated Feb. 5, 2013.
Patent Examination Report No. 1 issued in Australian Application No. 2009268453 on Oct. 11, 2013.
PCT/US2016/050005 International Search Report and Written Opinion dated Nov. 7, 2016.
European Patent Application No. 17188854.8 Extended Search Report dated Feb. 27, 2018.
McCray and Balaban, "The Gourmet Colon Prep," Nutrition Issues in Gastroenterology, Series #56, Practical Gastroenterology, Nov. 2007, 41-57.
PCT/US2016/050005 International Preliminary Report on Patentability dated Mar. 6, 2018.
U.S. Appl. No. 15/085,363 Office Action dated Sep. 26, 2017.
U.S. Appl. No. 15/611,390 Office Action dated Aug. 23, 2018.
U.S. Appl. No. 15/756,922 Restriction Requirement dated Oct. 5, 2018.
European Patent Application No. 15785236.9 First Examination Report dated Jan. 29, 2019.

* cited by examiner

FOODS, SYSTEMS, METHODS, AND KITS FOR PROVIDING ELECTROLYTE REPLACEMENT

CROSS-REFERENCE

This application is a divisional of U.S. patent application Ser. No. 14/699,973 entitled "FOODS, SYSTEMS, METHODS, AND KITS FOR PROVIDING ELECTROLYTE REPLACEMENT" filed Apr. 29, 2015, which claims the benefit of U.S. Provisional Application No. 61/986,048, filed Apr. 29, 2014, and U.S. Provisional Application No. 62/141,758, filed Apr. 1, 2015, the content of which each application is incorporated herein by reference in its entirety.

BACKGROUND

Laxatives may be taken by a subject for a number of reasons. Laxatives are, for example, prescribed for certain medical indications such as the cleansing of the GI tract in preparation for a medical or surgical procedure.

Laxatives may cause diarrhea in a subject which in turn may cause electrolyte loss and acid-base imbalance.

There are numerous types of laxatives, which have a number of different mechanisms of action. Polyethylene glycol, which is also known as PEG, is an osmotic laxative that is used for irrigation of the colon and GI tract in preparation for medical and surgical procedures. A bowel preparation regimen may, for example, prescribe the ingestion of PEG by a subject until the subject passes watery yellow or clear stools. Such watery yellow or clear stools in a subject are essentially diarrhea, and may be associated with electrolyte loss and acid-base imbalance. When subjects preparing for a medical or surgical procedure either fast or eat only liquids in addition to taking a laxative, the effect of a laxative induced electrolyte loss and acid-base imbalance is typically even more significant.

PEG-3350 is sold in the U.S. in laxative compositions that typically are to be combined with a liquid solution. Examples of such products include MIRALAX® from Schering-Plough; GOLYTELY®, NULYTELY®, and HALF-LYTELY® from Braintree Laboratories Inc. (Braintree, Mass.); and the fruit flavored COLYTE® from Schwarz Pharma, Inc. (Mequon, Wis.). Liquid formulations of PEG are inconvenient, unsatisfying, and uncomfortable to the consumer, and can cause undesirable mouth-feel, and/or create a bloated, overwhelmed feeling in the consumer's stomach.

SUMMARY

A subject may take an over the counter laxative, or be prescribed a laxative for a number of reasons including, for example, to prepare for a medical or surgical procedure. Preparation for a medical or surgical procedure typically requires a purging of the colon and GI tract in order to, for example, ensure optimal visibility on colonoscopy. An estimated 17.5 million Americans undergo colonoscopy yearly. The traditional bowel preparation for colonoscopy (and other invasive GI surgical and radiologic procedures) typically involves the subject drinking a large volume of water in which a laxative and electrolytes are dissolved. Traditional bowel preparations typically further involve eating no solid food the entire day before the procedure. Many subjects consider the traditional bowel preparation to be highly unpleasant.

Generally, effective provision of a laxative presents certain challenges. For example, laxative intake as part of a bowel preparation is associated with electrolyte loss through the GI tract and electrolyte imbalance. With respect to the traditional bowel preparation, because of the significant unpleasantness of the preparation, high numbers of patients in need of colonoscopy either avoid the procedure altogether or are not fully compliant with the preparation leading to inadequate visualization during the procedure due to retained stool within the colon. Described herein are compositions, methods, systems, and kits directed to overcoming at least the above two challenges associated with providing a laxative to a subject, by namely, replenishing electrolytes and improving the bowel preparation experience to increase compliance.

Described herein are food bars comprising more than 50% by weight of PEG-based laxatives, for example, PEG-3350, as well as methods of making and using the same.

In an embodiment, food bars comprise more than 50% by weight of a polyethylene glycol (PEG)-based laxative, for example, PEG-3350. In an embodiment, the food bars described herein include rice syrup. In an embodiment, the food bars described herein include about 25% to about 40% by weight of rice syrup. In an embodiment, the food bars described herein include coconut oil. In an embodiment, the food bars described herein include about 1.5% to about 3.0% by weight of coconut oil. In an embodiment, the food bars described herein include glycerin. In an embodiment, the food bars described herein include about 1.0% to about 3.0% by weight of glycerin.

In an embodiment, the food bars described herein include a flavorant, for example, a lemon, mint, ginger, garlic, pepper or caramel flavorant. In some embodiments, the food bars described herein include electrolytes, for example, sodium chloride, potassium chloride, potassium bicarbonate, or magnesium chloride.

Described herein are also methods of administering a laxative to a subject by providing the subject with the food bars described herein.

Described herein are also methods of inducing a bowel movement in a subject by providing the subject with the food bars described herein.

Described herein are also methods of making PEG-based laxative-containing food bars. A method of making PEG-based laxative-containing food bars comprises (1) mixing a PEG laxative powder with dry ingredients, for example, sea salt or flavor powders; (2) blending the PEG and dry ingredient mixture with melted coconut oil and glycerin, preferably at room temperature, for example, a temperature below 80° F. (26.7° C.), to form a homogenous malleable semi-solid mixture (for example, a fondant-like mass); (3) blending the malleable semi-solid mixture with rice syrup to form a homogeneous dispersion; (4) optionally folding additional ingredients, for example, rice crisps, dried fruit, or chocolate chips, into the dispersion; and (5) forming the dispersion into a bar, for example, of about 35 or 70 grams.

Described herein are compositions, methods, system, and kits for purging the GI tract of a subject while replenishing electrolyte losses and preventing electrolyte imbalance. In an embodiment, a food item comprises a plurality of food ingredients mixed with 1-3,000 milligrams of sodium, 1-3,000 milligrams of potassium, 1-750 ml of water, and 5-150 grams of a laxative. The plurality of food ingredients may comprise at least one grain, at least one of meat or fish, and/or at least one starch. The laxative may comprise PEG, which may further comprise PEG 3350, and PEG 3350 may comprise at least 50% by weight of said mixture. The food item may comprise a solid or a semi-solid food. A semi-solid food item may comprise 90% or less liquid by weight. The food item may comprise a bar and/or the food item may comprise a meal.

In another embodiment, a purgative system comprises a plurality of food items, wherein one or more food items comprise a plurality of ingredients mixed with one or more of a laxative and a salt, and wherein said plurality of food items collectively comprise 3000-11500 milligrams of sodium, 750-4000 milligrams of potassium, 2000-4000 ml of water, and 5-150 grams of a laxative.

The plurality of food ingredients may comprise at least one grain, at least one of meat or fish, and at least one starch. The laxative may comprise PEG, which may further comprise PEG 3350, and PEG 3350 may comprise at least 50% by weight of said mixture. The food item may comprise a solid or a semi-solid food. A semi-solid food item may comprise 90% or less liquid by weight. The plurality of food items may comprise between 1 and 10 solid food items. The purgative system or kit may further comprise at least four liters of water. The plurality of food items may comprise bars and/or the plurality of food items may comprise one or more meals. The purgative system or kit may further comprise an instruction to eat no other food items in addition to said plurality of food items during a 36 hour period before a medical or surgical procedure. The plurality of food items may collectively comprise about 600 to 3,000 calories.

In another embodiment, a method for replacing electrolytes lost by a subject due to ingesting a laxative, said method comprises providing to said providing to said subject either one food item or a plurality of food items, wherein either said one food item comprises a plurality of food ingredients mixed with 1-3,000 milligrams of sodium, 1-3,000 milligrams of potassium, 1-750 ml of water, and 5-150 mg of a laxative, or at least one food item of said plurality of food items comprises a plurality of ingredients mixed with 1-3,000 milligrams of sodium, 1-3,000 milligrams of potassium, 1-750 ml of water, and 5-150 grams of a laxative. The method may further comprise providing to the subject an instruction to consume said one or more food items during a 36 hour period before a medical or surgical procedure. The laxative may comprise PEG, which may further comprise PEG 3350, and PEG 3350 may comprise at least 50% by weight of said mixture. The one food item or the plurality of food items may comprise a solid or a semi-solid food. A semi-solid food item may comprise 90% or less liquid by weight. The plurality of food items may comprise between 1 and 10 solid food items. The method may further comprise providing to the subject at least four liters of water during a 36 hour period before a medical or surgical procedure. The one food item or the plurality of food items may be provided to the subject during a 36 hour period before a medical or surgical procedure. The one food item may comprise a bar or the plurality of food items may comprises bars. The one food item may comprise a meal. The plurality of food items may comprise one or more meals. The one food item alone or the plurality of food items may collectively comprise about 600 to 3,000 calories.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the described subject matter are set forth with particularity in the appended claims. A better understanding of the features and advantages of the described subject matter will be obtained by reference to the following detailed description that sets forth illustrative embodiments, in which the principles of the described subject matter are utilized, and the accompanying drawings of which:

DETAILED DESCRIPTION OF THE INVENTION

Described herein are compositions, methods, system, or kits for purging the GI tract of a subject while replenishing electrolyte losses and preventing electrolyte imbalance. Before explaining at least one embodiment of the inventive concepts disclosed herein in detail, it is to be understood that the inventive concepts are not limited in their application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for purpose of description only and should not be regarded as limiting in any way.

In the following detailed description of embodiments of the described subject matter, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

The terms "replace" and "replenish" are used in reference to electrolytes. Both terms are essentially interchangeable when used in reference to electrolytes and indicate that electrolytes that are lost are given back.

The term "electrolyte" or "electrolytes" may refer to a quantity sufficient to replace or replenish electrolyte loss. "Electrolytes" may refer to a plurality of types of electrolytes or a quantity of one electrolyte.

Further, unless expressly stated to the contrary, "or" refers to an inclusive or and not an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

The term "subject" as used herein may refer to a human subject or any animal subject.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Laxatives may be used for a number purposes including to, for example, prepare the GI tract of a subject for a medical or surgical procedure. Bowel preparation for both surgical and medical procedures requires that the subject fully purge their GI tract of food and stool prior to the procedure. For surgical procedures involving bowel resection, a GI tract free of food and stool is believed to improve anastomotic healing. For medical procedures such as endoscopy, a GI tract free of food and stool is critical for effective visualization of anomalies and growths.

The purging of the GI tract to prepare the GI tract of a subject for a medical or surgical procedure may take place over a period of time of, for example, 18 to 36 hours prior to a surgical or medical procedure. During the period of preparation, subjects may be instructed to ingest a quantity of PEG sufficient to produce multiple bowel movements over this period. Due to the osmotic mechanism of PEG, subjects typically experience significant diarrhea over the period of time that PEG is ingested and is active. Diarrhea causes electrolyte losses directly from the GI tract that, depending on the severity of the diarrhea experienced, may lead to from mild to severe electrolyte imbalances in a subject who has ingested PEG as part of a bowel preparation for a surgical or medical procedure.

Generally, laxatives are associated with electrolyte loss from the GI tract with accompanying electrolyte imbalance. Electrolytes may be lost from the GI tract when, for example, the laxatives cause diarrhea with accompanying fluid shifts. Electrolyte imbalance may be a serious condition and may cause side effects ranging from nausea to seizure and cardiac arrest.

Non-limiting examples of electrolytes lost by a subject due to the actions of laxatives include sodium, potassium, chloride, and bicarbonate. Additionally, bicarbonate is the conjugate base of carbonic acid and a major acid buffer in a subject. Thus, bicarbonate loss is associated with acidosis as well.

To facilitate effective colonic cleansing using laxatives and protect the health of subjects undergoing a bowel preparation prior to a medical or surgical procedure, a laxative may be provided to a subject together with a quantity of electrolytes sufficient to replenish any electrolytes lost by the subject due to the action of the laxative. Replacing lost electrolytes over the period in which a laxative is administered will prevent electrolyte imbalance and acidosis in a subject along with the associated negative side effects. Acidosis is associated with lethargy, shortness of breath, and organ injury in more severe cases.

Many subjects find that drinking an aqueous solution of electrolytes, in quantities sufficient to replace GI losses due to the actions of a laxative, to be difficult, because solutions comprising electrolytes in quantities sufficient to replace GI losses are associated with a bad taste. Thus, for example, many subjects fail to comply with bowel preparation regimens that require a subject to replenish electrolytes by drinking large volumes of electrolytes dissolved in water.

Traditional bowel preparation regimens such as Golytely™ provide the laxative polyethylene glycol (PEG) along with electrolytes dissolved together in a volume of water. Golytely™ is reported to have a very unpleasant taste. The poor taste of Golytely™ is caused in significant part by the electrolytes in the prep solution. Poor taste leads to poor compliance with the Golytely™ regimen. Poor compliance with the regimen both means that electrolytes are not replenished and insufficient laxative is ingested by the subject. Poor electrolyte replenishment leads to electrolyte imbalance and acidosis in the subject, and poor intake of laxative leads to inadequate preparation for medical and surgical procedures. Electrolyte imbalance may cause complications including, for example, dizziness, seizure, and cardiac arrest, and poor bowel preparation may lead to surgical complication and misdiagnosis or require the subject to undergo a new preparation with rescheduling of the procedure.

Typically, traditional bowel preparation regimens require a subject to take in only liquids during the period of the bowel preparation. That is, typically, subjects are placed on a liquid only diet during the period of the bowel preparation. Subjects are placed on the liquid only diet during the period of bowel preparation, because it is generally believed that subjects must be maintained on a liquid diet in order achieve an adequately prepared GI tract. However, if subjects are required to be on a liquid only diet, the available means for delivering replacement electrolytes and laxative to the subject are limited. That is, to comply with a liquid only diet requirement, electrolyte replacement may only be provided to a subject in aqueous solution. As explained, the traditional aqueous solution mode of delivery of replacement electrolytes and laxative does not promote a high degree of compliance in subjects.

An improvement in compliance and subject satisfaction with electrolyte replacement will occur with an improvement in the experience of ingesting the quantity of electrolytes necessary for replacing electrolytes lost due to the actions of the laxative. That is, an improvement in the mode of delivery of electrolyte replacement to subjects taking a laxative, will improve compliance thus avoiding electrolyte imbalance and inadequate preparation of the GI tract.

An improvement in the mode of delivery of replacement electrolytes is achieved when subjects need not be limited to drinking replacement electrolytes in aqueous solution. Eliminating the liquid diet only requirement in bowel preparations may be achieved, because using real food does not affect the quality of the bowel preparation. Thus, replacement electrolytes both with and without laxative may be delivered effectively to a subject via good tasting food items. The ingredients in the food items either overcome or substantially reduce the bad taste associated with quantities of electrolytes used to replace electrolytes lost due to the actions of a laxative. The improved taste and texture of food items as opposed to aqueous solution greatly improves subject compliance and satisfaction. For example, shakes, smoothies, and other beverages containing replacement electrolytes are advantageous means for delivering replacement electrolytes, because, for example, shakes, smoothies, and beverages may be configured to provide higher replacement electrolyte concentrations while effectively reducing or eliminating the bad taste associated with high concentrations of electrolytes. Thereby, for example, shakes, smoothies, and other beverages containing replacement electrolytes increase patient compliance with bowel preps.

Described herein are methods, compositions, system or kits, and kits that effectively deliver a laxative to a patient along with effective electrolyte replenishment by delivering both a laxative and electrolytes via a food item. The food item is prepared by one or more of combining, mixing, or integrating the ingredients that form the food item together with one of or both of a laxative and electrolytes so that the ingredients in the food item either eliminate or significantly reduce the poor taste associated with either the electrolytes or the laxative.

In an embodiment, a food item is prepared by mixing together food ingredients with one or more of a laxative and replacement electrolytes so that, once prepared, the food item contains one or more of the laxative and the replacement electrolytes.

In an embodiment the food item is a low fiber food. Non-limiting examples of low fiber foods include products made with refined grains, strained vegetable juice, potatoes without skin, eggs, fish, pudding, and an assortment of beverages. Food items described herein may be prepared from low fiber, low residue ingredients. Table I provides an exemplary listing of foods allowed and excluded from a low fiber/low residue diet. One of skill in the art will readily be able to identify other foods that can be used, and those that should be avoided.

TABLE I

| Food Group | Allowed | Excluded |
| --- | --- | --- |
| Starch | Cereals, rice, pasta, and other products made with refined grains | Whole grain cereals, rice, pasta, legumes, and popcorn |
| Vegetables | Strained vegetable juices, Potatoes without skins | All vegetables |
| Fruits | Fruit juices except prune | All fruits including canned |
| Dairy | Limited to 2 cups per day including yogurts, smoothies, puddings and strained cream soups | Whole milk/cream or foods made with them; cheese |
| Meats/Meat Substitutes | Eggs, fish, (tofu) | Beef, pork, chicken, processed meats, dried peas/beans, peanut butter |
| Desserts | Gelatin, pudding, sherbet, sorbet, custards, plain cake (angel food), plain cookies (sugar), yogurt, smoothies | All pastries plus desserts that contain skins, nuts, seeds and raisins |
| Beverages | Coffee and tea (limited), non-cola sodas, pulp free fruit juices, pulp free fruit ice white ice tea, non-caloric teas and beverages, freezer pops, milk (limited intake), smoothies, protein drinks | |
| Miscellaneous | | Nuts, seeds |

In an embodiment, the food item may be a solid, liquid, or semi-solid food. Non-limiting examples of solid food items that contain a laxative and electrolytes include cookies, bars, brownies, and pancakes. Non-limiting examples of liquid foods include shakes, juices, teas, and coffees. Non-limiting examples of semi-solid foods include lasagna, yogurt, pasta with sauce, and meat with sauce. In an embodiment, a semi-solid food item comprises between 10% and 90% liquid.

In a preferred embodiment the laxative present is sufficient to induce one or more bowel movements in the subject and the electrolytes present are sufficient to replace any electrolyte losses due to the laxative.

In an embodiment, a food item comprises a food bar. In an embodiment, a food bar comprises more than 50% by weight of PEG-based laxatives. Any food- or pharmaceutical-grade PEG polymer may be employed in the compositions contemplated herein. PEG polymers having an average molecular weight of at least 1000 (and generally no greater than 20,000) are exemplary, while an average molecular weight between about 3000 and 9000 is preferred. In some embodiments, the laxative agent is PEG-3350. In an embodiment, the dose of the laxative provided in each bar should be sufficient to induce a bowel movement.

In an embodiment, a food bar comprises more than 50% by weight of PEG-based laxatives, for example, PEG-3350. The food bars described herein are formulated to contain a maximum amount of PEG (for example, 50% or more, for example, up to 40 grams in a typical 70 g bar) in a single bar while still providing a reasonable bar size, permitting comfortable consumption in a single snack or meal. The improved taste and the convenience of the food bars described herein can boost patient compliance and increase efficacy. In an embodiment, a food bar comprises less than 50% by weight of PEG-based laxatives, for example, PEG-3350. In an embodiment, a food bar containing a PEG-based laxative further comprises replacement electrolytes as described herein.

In an embodiment, a food bar is made without excessive heating of PEG, for example PEG-3350, such that no significant breakdown of the PEG occurs. Accordingly, the present inventors have specially formulated the binding system to ensure no heating is required to produce the bars. The innovative binders used in making the bars can reduce the sweetness in the final product and improve the taste of the bars. Flavorants such as lemon, mint, ginger, garlic, pepper, chocolate, vanilla, or caramel can be added to the bars described herein to mask the taste of PEG and to complement (lemon, mint, ginger, garlic, pepper) or disguise (chocolate, vanilla, or caramel) the cooling effect of PEG when dissolved in the mouth, and/or to accommodate a high level of electrolytes. In some bars, crisps, for example, rice crisps or sorghum crisps can be added to provide an alternate texture.

In an embodiment, the dose of laxative provided in each bar is sufficient to induce a bowel movement. In an embodiment, the dose of laxative provided in each bar is insufficient to induce a bowel movement, and the dose becomes sufficient once the bar is provided to a subject together with additional laxative. For example, a bar and a shake that are provided to a subject may both contain a quantity of laxative that when taken together comprises an amount that is sufficient to cause a bowel movement in the subject. In an embodiment, a laxative with sufficient laxative to induce a bowel movement is provided together with a shake that contains a quantity of electrolytes sufficient to replace a quantity of electrolytes lost by the subject due to the actions of the laxative in the bar. In an embodiment, a bar contains a dose of laxative sufficient to induce a bowel movement in a subject along with a quantity of electrolytes sufficient to replace a quantity of electrolytes lost by the subject due to the actions of the laxative in the bar. In an embodiment, a bar is provided to a subject together with a shake, wherein the shake contains a dose of laxative sufficient to induce a bowel movement in a subject and the bar contains a quantity of electrolytes sufficient to replace a quantity of electrolytes lost by the subject due to the actions of the laxative in the shake.

In addition, the ingredients used in these bars for bowel prep are preferably low in fat (i.e., less than 15 grams of fat per day or prep period) and bland colored (for example, white, cream, yellow, or clear) to allow for adequate colon cleansing.

In some embodiments, the food bars described herein include PEG-3350, rice syrup, coconut oil, and glycerin. In some embodiments, the food bars described herein include at least 50% (for example, about 50%, 51%, 52%, 53%, 54%, 55%, 56%, 57%, 58%, 59%, 60%, 65%, 70%, 75%, 80%, 85%) by weight of PEG-3350. In some embodiments, the food bars described herein include about 25% to about 40% by weight of rice syrup (for example, about 25%, 26%, 27%, 28%, 29%, 30%, 31%, 32%, 33%, 34%, 35%, 36%, 37%, 38%, 39%, 40%); or, as an alternative to or substitute for all or part of the rice syrup, barley syrup, barley malt syrup, maple syrup, molasses, honey, agave syrup, or corn syrup can be used. In some embodiments, the food bars described herein include about 1.5% to about 3.0% by weight of coconut oil (for example, about 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%); or, as an alternative to or substitute for all or part of the coconut oil, lard, vegetable shortening, palm oil, cocoa butter, butter, or margarine, can be used. In some embodiments, the food bars described herein include about 1.0% to about 3.0% by weight of glycerin (for example, about 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%); or, as an alternative to or substitute for all or part of the glycerin, corn syrup or vegetable oil can be used.

In some embodiments, the food bars described herein include at least one flavorant, for example, a lemon flavorant, a mint flavorant, a ginger flavorant, a pepper flavorant, a vanilla flavorant, or a caramel flavorant. Several types of chocolates can be added to the food bars described herein, for example, white chocolate, dark chocolate, milk chocolate, semi-sweet chocolate, sweet chocolate, hard chocolate, soft chocolate, bitter chocolate, Cocoa mass, cocoa butter mix, and hard boiled toffees.

In an embodiment, the food bars described herein include sugar or another sweetener, for example, a sweetener may comprise aspartame, cyclamate, saccharin, stevia, sucralose, mogrosides, lactose, sorbitol, acesulfame potassium, isomalt, mannitol, dextrose, glucose, fructose, honey, or high fructose syrup.

In some embodiments, the food bars described herein include salt. In some embodiments, the food bars described herein include citric acid or citrate. In some embodiments, the food bars described herein include a coating, for example, a yogurt coating.

In some embodiments, the food bars described herein includes an electrolyte, for example, sodium chloride, potassium chloride, potassium bicarbonate, or magnesium chloride.

In some embodiments, the food bars described herein includes one or more preservatives, such as sodium benzolate, ascorbyl palmitate, sorbic acid, BHT or EDTA, to increase the shelf life of the final products. The preservatives employed in the food bars of the invention generally range from about 0% to about 5% by weight of the total weight of the food bars.

Generally, food items used may comprise ingredients that are flavorful and taste good so that the bad taste of the electrolytes in the food is overcome by the taste of the food itself. If the food item containing laxative and electrolytes is used as part of a bowel preparation regimen compliance with the regimen will increase due to the elimination or reduction of the bad taste caused by the replacement electrolytes. In an embodiment, the flavor of the food conceals the bad taste of the electrolytes. In an embodiment, the flavor of the food conceals the bad taste of the laxative as well as the electrolyte. In an embodiment, the flavor of the food is achieved by adding seasonings. Non limiting examples of seasonings are herbs and spices. In an embodiment, the flavor is achieved by adding a natural flavoring substance. A natural flavoring substance may be obtained from plant or animal raw materials, by physical, microbiological or enzymatic processes. In an embodiment, the flavor is achieved by adding a nature-identical flavoring substance. Nature-identical flavoring substances may be obtained by synthesis or isolated through chemical processes, which are chemically identical to flavoring substances naturally present in products intended for human consumption. In an embodiment, the flavor is achieved by adding an artificial flavoring substance. Artificial flavoring substances may typically be produced by fractional distillation and additional chemical manipulation of naturally sourced chemicals. One having skill in the art will know that there numerous examples of natural, nature-identical, and artificial flavors. Ingredients such as, for example, melted coconut oil, rice syrup, and glycerin may be blended into a mixture to add both thickness and flavor. Additional ingredients, for example, rice crisps, dried fruit, or chocolate chips may be added. Different flavors and different flavoring types may be used either alone or in combination to provide flavors that make a food containing an unsavory element, such as, for example, a replacement load of electrolytes, palatable by masking the unsavory element or elements.

In an embodiment, a food item contains a sufficient quantity of laxatives that when ingested by a subject causes the subject to produce a yellowy or clear liquid effluent stool. In an embodiment one or more food items contain electrolytes in a quantity sufficient to replenish electrolyte losses in the subject due to the actions of the laxative. Non-limiting examples of electrolytes contained in the food items include sodium sulfate, sodium bicarbonate, sodium chloride; and potassium chloride.

The laxative used may be PEG or any other laxative type. If PEG is used, PEG 3350 may be used as the laxative. PEG is available in powder form which is a convenient form to mix together with food ingredients when preparing the food item containing PEG and electrolytes.

The food items containing laxative described herein are preferably prepared without excessive heating of the laxatives therein. For example, the food items may be prepared so that the laxative is not heated above 80° F. In some embodiments, once the laxative has been added or is present and the mixture is maintained at a temperature sufficiently low to prevent the formation of PEG breakdown products, for example, below 100° F., below 95° F., below 90° F., below 85° F., below 80° F., below 75° F., below 70° F., below 65° F., below 60° F., below 55° F., and below 50° F.

Laxatives such as, for example, PEG are available in powder form which may be convenient for mixing together with both dry and wet ingredients.

The food bars described herein are preferably made without excessive heating of the laxatives therein, for example, by a method that does not include heating the PEG above 80° F. In some embodiments, the methods include (1) mixing a PEG laxative powder with dry ingredients, for example, sea salt or flavor powders; (2) blending the PEG and dry ingredient mixture with melted coconut oil and glycerin, preferably at room temperature, for example, a temperature below 80° F. (26.7° C.), to form a homogeneous semi-solid mixture (for example, a fondant-like mass); (3)

blending the semi-solid mixture with rice syrup to form a homogeneous dispersion; (4) optionally folding additional ingredients, for example, rice crisps, dried fruit, or chocolate chips, into the dispersion; and (5) forming the dispersion into a bar, for example, of about 35 or 70 grams. In some embodiments, once the PEG has been added or is present, the methods are performed at, or include maintaining the mixture and dispersion at, a temperature sufficiently low to prevent the formation of PEG breakdown products, for example, below 100° F., below 90° F., below 80° F., below 75° C., below 70° C., below 65° C., below 60° C., below 55° C., below 50° C., below 45° C., below 40° C., below 35° C., or below 30° C. The dispersion can be, for example, extruded to form a sheet for die cutting, or into individual bars of the desired shape and size, using any suitable extruding apparatus known in the art.

The laxative agents can be incorporated in the bars by any method including mixing in as an ingredient, and/or by inclusion in or as a coating, topping, or glaze.

Prior to packaging the food bars described herein, the food bars may, optionally, be irradiated in order to kill microorganisms that may have contaminated the food bars during their preparation. Such irradiation should not diminish the effectiveness of the PEG-based laxatives contained therein.

The resulting food bars may then be packaged in any manner known by those of skill in the art for packaging food bars. The preferred method of packing the food bars is by hermetically sealing each food bar within a film having oxygen barrier properties, such as a foil laminate, purging the inner space of the wrapper with nitrogen (to create a nitrogen blanket), placing a group of the wrapped food bars in an aluminum can, having the air present in the aluminum can removed with a vacuum, and replacing the removed air with nitrogen. When packaged in this manner, the food bars described herein have a shelf life at normal room temperature (from about 59° F. to about 86° F.) of about two years. In an embodiment, food bars packaged in the manner described herein have a shelf life at normal room temperature of about six months to a year. In some embodiments, a kit is provided that includes the food bars described herein as a snack or meal. In some embodiments, the kit also includes other food and/or beverages that the subject will consume. The kit can also include instructions for use in a method described herein. In some embodiments, the food bars are provided in prepackaged form, for example, packed in a container, for example, in a shelf stable, refrigerated, or frozen form. The food bars can be purchased, for example, from a pharmacy or other retail outlet.

Electrolytes may be combined with one or more of a laxative and a plurality of food ingredients as a salt or the electrolytes may be dissolved in solution. Electrolytes may be combined with food ingredients so that a food item may be prepared so that, once prepared, the food item, for example, contains a laxative along with 1-3,000 milligrams of sodium, 1-3,000 milligrams of potassium, or 1-750 ml of water.

For example, a serving of lasagna may be prepared by combing lasagna ingredients such as, for example, noodles and sauce, with laxative along with 1-3,000 milligrams of sodium, 1-3,000 milligrams of potassium, or 1-750 ml of water. The prepared lasagna containing the laxative and replacement electrolytes serves as the medium for delivering the laxative and electrolytes to the subject, and the flavoring provided by the food ingredients that are intermixed with the laxative and replacement electrolytes either eliminate or greatly reduce the poor taste associated with laxative and/or electrolytes.

Exemplary quantities of electrolyte salts that may be added either together or separately to one food item or more than one food item in order to replenish electrolytes lost by a subject taking a laxative may be further seen in table II.

TABLE II

| Compound Name | Approximate Quantity Added in Grams |
| --- | --- |
| Sodium sulfate | 20-30 |
| Sodium bicarbonate | 6-7 |
| Sodium chloride | 5-6 |
| Potassium chloride | 2-3 |

Exemplary quantities of electrolytes, water, and laxative contained in either one food item or collectively in a number of food items, such as the collective food items in a system or kit, may be found in table III and table IV respectively.

TABLE III

| Individual Items | | | | |
| --- | --- | --- | --- | --- |
| Food Item | Sodium (mg) | Potassium (mg) | Water (ml) | PEG (gm) |
| Solid item | 1-3000 | 1-1000 | 1-750 | 0-150 |
| Semi-Solid item | 1-3000 | 1-1000 | 1-750 | 0-150 |
| Liquid item | 1-3000 | 1-1000 | 1-750 | 0-150 |

TABLE IV

| Complete Kit | | | | |
| --- | --- | --- | --- | --- |
| Food Item | Sodium (mg) | Potassium (mg) | Water (ml) | PEG (gm) |
| Kit | 3000-11500 | 750-4000 | 2000-4000 | 200-420 |

In an embodiment, the laxative used may be PEG and may further be PEG 3350. The PEG 3350 may have a weight of about 5-300 grams. Thus for example, a serving of lasagna weighing a total of 500 grams may contain 150 grams of laxative.

In an embodiment, the weight of the laxative makes up at least 95% of the weight of the food item. In an embodiment, the weight of the laxative makes up at least 90% of the weight of the food item. In an embodiment, the weight of the laxative makes up at least 85% of the weight of the food item. In an embodiment, the weight of the laxative makes up at least 80% of the weight of the food item. In an embodiment, the weight of the laxative makes up at least 75% of the weight of the food item. In an embodiment, the weight of the laxative makes up at least 70% of the weight of the food item. In an embodiment, the weight of the laxative makes up at least 65% of the weight of the food item. In an embodiment, the weight of the laxative makes up at least 60% of the weight of the food item. In an embodiment, the weight of the laxative makes up at least 55% of the weight of the food item. In an embodiment, the weight of the laxative makes up at least 50% of the weight of the food item. In an embodiment, the weight of the laxative makes up at least 45% of the weight of the food item. In an embodiment, the weight of the laxative makes up at least 40% of the weight of the food item. In an embodiment, the weight of the laxative makes up at least 35% of the weight of the food item. In an embodiment the weight of the laxative makes up at least 30% of the weight of the food item. In an embodiment, the weight of the laxative makes up at least 25% of the weight of the food item. In an embodiment, the weight of the laxative makes up at least 20% of the weight of the food item. In an embodiment, the weight of the laxative makes up at least 15% of the weight of the food item. In an embodiment, the weight of the laxative makes up at least 10% of the weight of the food item. In an embodiment, the weight of the laxative makes up at least 5% of the weight of the food item.

In an embodiment, a food item may comprise a bar similar to a candy bar or other dessert bar or a protein bar. In an embodiment, a food item may comprise a meal such as, for example, a serving of pasta with sauce.

In an embodiment, a food item containing a laxative and electrolytes may comprise, for example, about 20 calories. In an embodiment, a food item containing a laxative and electrolytes may comprise, for example, about 40 calories. In an embodiment, a food item containing a laxative and electrolytes may comprise, for example, about 80 calories. In an embodiment, a food item containing a laxative and electrolytes may comprise, for example, about 100 calories. In an embodiment, a food item containing a laxative and electrolytes may comprise, for example, about 150 calories. In an embodiment, a food item containing a laxative and electrolytes may comprise, for example, about 200 calories. In an embodiment, a food item containing a laxative and electrolytes may comprise, for example, about 250 calories. In an embodiment, a food item containing a laxative and electrolytes may comprise, for example, about 300 calories. In an embodiment, a food item containing a laxative and electrolytes may comprise, for example, about 350 calories. In an embodiment, a food item containing a laxative and electrolytes may comprise, for example, about 400 calories. In an embodiment, a food item containing a laxative and electrolytes may comprise, for example, about 450 calories. In an embodiment, a food item containing a laxative and electrolytes may comprise, for example, about 550 calories. In an embodiment, a food item containing a laxative and electrolytes may comprise, for example, about 600 calories. In an embodiment, a food item containing a laxative and electrolytes may comprise, for example, about 650 calories. In an embodiment, a food item containing a laxative and electrolytes may comprise, for example, about 700 calories. In an embodiment, a food item containing a laxative and electrolytes may comprise, for example, about 750 calories. In an embodiment, a food item containing a laxative and electrolytes may comprise, for example, about 800 calories. In an embodiment, a food item containing a laxative and electrolytes may comprise, for example, about 850 calories. In an embodiment, a food item containing a laxative and electrolytes may comprise, for example, about 900 calories. In an embodiment, a food item containing a laxative and electrolytes may comprise, for example, about 1000 calories.

In an embodiment, a system or kit for purging the GI tract of a subject while replenishing electrolytes comprises a plurality of food items. A plurality of food items may comprise, for example, 2 to 10 food items that are provided for a subject to consume while preparing for a medical or surgical procedure. The system or kit may comprise of multiple meals such as breakfast, lunch, and dinner. In an embodiment the food is a low fiber food. The food may be a solid, liquid, or semi-solid food. Non-limiting examples of solid foods that contain a laxative and electrolytes include cookies, bars, brownies, and pancakes. Non-limiting examples of liquid foods include shakes, juices, teas, and coffees. Non-limiting examples of semi-solid foods include lasagna, yogurt, pasta with sauce, and meat with sauce.

One or more food items within the system or kit may be identical, or one or more food items may be different. Similarly, one or more food items within the system or kit may contain replacement electrolytes only, one or more food items within the system or kit may contain laxative only, one or more food items in the system or kit may contain replacement electrolytes and laxative, and one or more food items within the system or kit may contain neither laxative or replacement electrolytes. Similarly, one or more food items within the system or kit may comprise replacement electrolytes that are identical in terms of type or quantity to the replacement electrolytes contained in one or more food items in the system or kit, and one or more food items within the system or kit may comprise replacement electrolytes that differ in term of type or quantity from replacement electrolytes contained in one or more food items within the system or kit. Similarly, one or more food items within the system or kit may comprise laxative that is identical in terms of type or quantity to the laxative contained in one or more food items in the system or kit, and one or more food items within the system or kit may comprise laxative that differs in term of type or quantity from the laxative contained in one or more food items within the system or kit.

For example, a food system or kit may comprise a 600 gram serving of lasagna and a 100 gram serving of pudding. In an exemplary embodiment, the lasagna and pudding may both comprise 6 grams of sodium bicarbonate. In an exemplary embodiment, the lasagna alone may comprise 6 grams of sodium bicarbonate and the pudding may comprise no replacement electrolytes. In an exemplary embodiment, the lasagna alone may comprise 6 grams of sodium bicarbonate and the pudding comprises 5 grams of sodium chloride. It should be understood that these examples are illustrative, and are not meant to limit the subject matter here described in any way. It should be further understood that many other possible combinations are achievable using the systems or kits described here.

For further example, the food items in the system or kit may also contain total amount of electrolyte replacement or laxative that collectively comprises a target quantity. For example, a system or kit may comprise a 600 gram serving of lasagna and a 100 gram serving of pudding. In an exemplary embodiment, the lasagna may comprise 5 grams of sodium bicarbonate and the pudding may comprise 1 gram of sodium bicarbonate, collectively totaling 6 grams of sodium bicarbonate within the system or kit. The collective delivery of electrolyte replacement or laxative is, for example, highly advantageous because it allows smaller more palatable quantities of electrolytes to be delivered within each food item and also helps to ensure that the electrolytes will be delivered throughout the course of the bowel preparation regimen in, for example, multiple meals. It should be understood that these examples are illustrative, and are not meant to limit the subject matter here described in any way. It should be further understood that many other possible combinations are achievable using the systems or kits described here.

Figure 1:
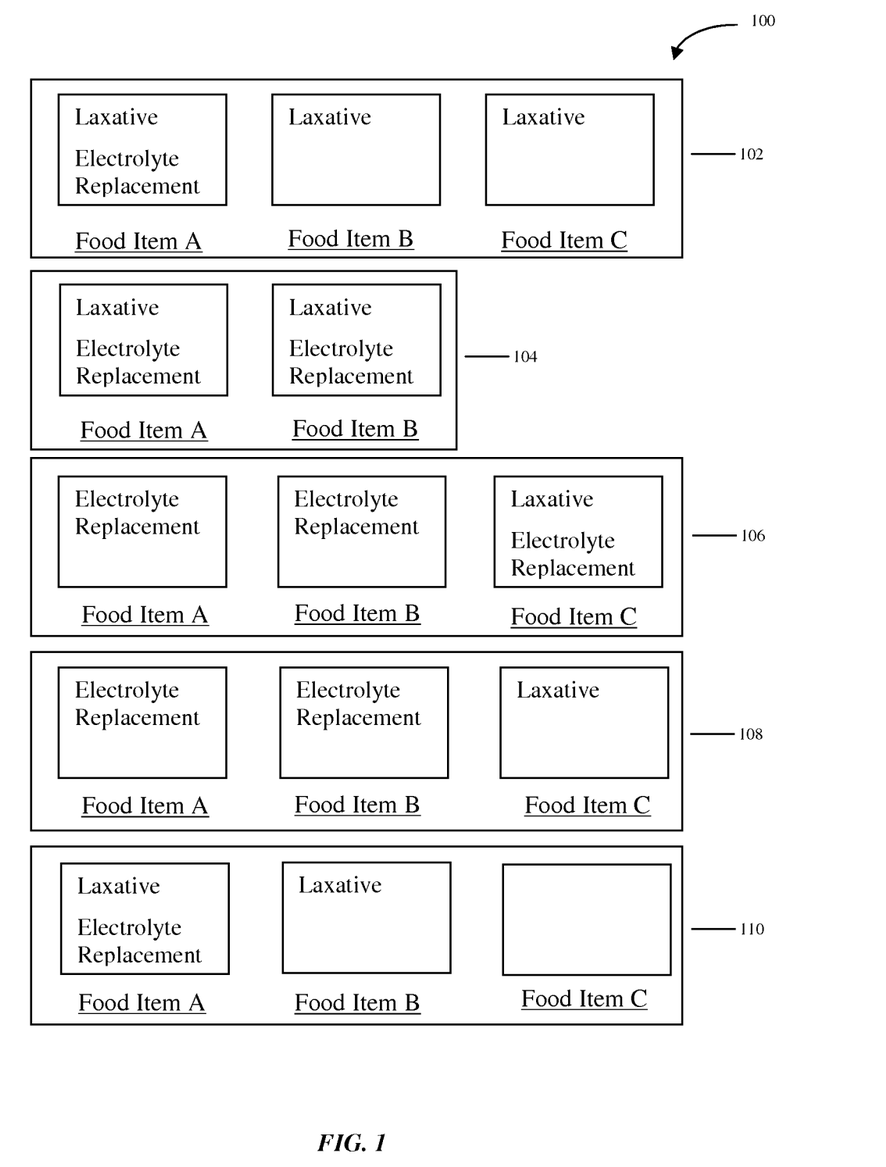
FIG. 1 shows a schematic representation of a number of non-limiting exemplary systems or kits each comprising different distributions of electrolyte replacement and laxative.

FIG. 1 shows a schematic representation of a number of non-limiting exemplary systems or kits each comprising different distributions of electrolyte replacement and laxative. An exemplary system or kit 102 comprises three food items, A, B, and C. In exemplary system or kit 102, food item A comprises laxative and electrolyte replacement, food item B comprises laxative, and food item C comprises laxative. An exemplary system or kit 104 comprises two food items, A and B. In exemplary system or kit 104, food item A comprises laxative and electrolyte replacement, and food item B comprises laxative and electrolyte replacement. An exemplary system or kit 106 comprises three food items, A, B, and C. In exemplary system or kit 106, food item A comprises electrolyte replacement, food item B comprises electrolyte replacement, and food item C comprises laxative and electrolyte replacement. An exemplary system or kit 108 comprises three food items, A, B, and C. In exemplary system or kit 108, food item A comprises electrolyte replacement, food item B comprises electrolyte replacement, and food item C comprises laxative. An exemplary system or kit 110 comprises three food items, A, B, and C. In exemplary system or kit 108, food item A comprises laxative and electrolyte replacement, food item B comprises laxative, and food item C comprises neither laxative nor electrolyte replacement.

It should be understood that the examples provided herein of the composition of the system or kit described apply in the same way to laxatives, and in no way are the examples meant to contain all the possible combinations and permutations of the system or kit described herein as it is understood that numerous combinations and permutations are possible. Likewise, it should be understood that food items may comprise laxatives together with replacement electrolytes or the food items may contain laxative alone or replacement electrolytes alone, as well as any other possible combinations and permutation of different replacement electrolytes in terms of quantity and type combined with different laxative in terms of quantity and type.

The system or kit may be provided to a subject to be ingested within a period of time comprising of, for example, 36 hours before a medical or surgical procedure. The system or kit may be provided to a subject to be ingested within a period of time comprising of, for example, 30 hours before a medical or surgical procedure. The system or kit may be provided to a subject to be ingested within a period of time comprising of, for example, 24 hours before a medical or surgical procedure. The system or kit may be provided to a subject to be ingested within a period of time comprising of, for example, 18 hours before a medical or surgical procedure. It should be understood that the above examples are exemplary only and the system or kits described here may be ingested over other periods of time.

The food items contained in the systems or kits described herein may be ingested at different times. That is, the entire system or kit need not be ingested at once. For example, a system may comprise of three food items, A, B, and C, wherein A, B, and C all contain a quantity of replacement electrolytes and laxative. Item A may, for example, be ingested at a time that is 18 hours from a scheduled medical or surgical procedure, item B may, for example, be ingested at a time 6 hours later, and item C may, for example, be ingested at a time 6 hours after ingestion of item B. In this way the laxative and electrolytes that are provided to the subject may be spread out over time. In this way, the quantity of bad tasting elements that a subject must ingest may be delivered over time. Using multiple food items to deliver the laxative and replacement electrolytes over time allows for smaller quantities of those elements to be in each item of the system or kit. When there is a relatively small quantity (compared to for example the traditional preparations) of laxative and replacement electrolytes in the individual food items, each item will be more palatable to a subject thus ensuring compliance with the regimen and proper electrolyte replacement.

In the example above that used food items A, B, and C to deliver electrolytes and laxative over the course of 18 hours, the electrolyte replacement and laxative delivery may be optimized. For example, laxative delivery may be arranged to produce the highest likelihood of compliance and proper cleansing of the bowel. For example, a larger laxative dose may be given initially with food item A with the laxative quantity tapering with later ingested items B and C. Electrolyte replacement is then provided in a way that will optimize electrolyte replacement. In general, electrolyte replacement may be optimized in, for example, electrolyte quantity and electrolyte absorption efficiency. That is, for example, the electrolyte replacement is spread throughout the items of the system or kit to match the actions of the laxative. For example, a larger laxative dose will be given contemporaneously or relatively contemporaneously with a larger electrolyte replacement dose so that the loss of electrolytes due to diarrhea losses can be replaced proportionally and effectively.

In a preferred embodiment, the system or kit collectively contains sufficient laxative to induce one or more bowel movements in the subject and the electrolytes present are collectively sufficient to replace any electrolyte losses due to the laxative. If used as a bowel preparation for a medical or surgical procedure the system or kit may collectively contain sufficient laxative to induce a yellowy or clear effluent stool in a subject, and sufficient electrolytes to replenish any electrolytes lost due to the action of the laxative.

The system or kit may, for example, comprise a plurality of foods. For example, the system or kit may comprise 1-10 solid food items, 1-10 semi-solid food items, or 1-10 liquid food items or all possible combinations or permutations thereof. The system or kit may comprise a plurality of meals. For example, the system or kit may comprise the meals of breakfast, lunch, and dinner.

For example, breakfast may comprise a breakfast bar comprising for example chocolate, peanut butter, and oats mixed with laxative and electrolytes. Breakfast may further comprise oatmeal mixed with electrolytes only. Lunch may comprise meatloaf with gravy containing both laxative and electrolytes. Lunch may further comprise a desert such as a pudding containing neither laxative or replacement electrolytes. Dinner may comprise lasagna with replacement electrolytes only. The exemplary system or kit described comprises of 5 total food items some items containing laxative only, some items containing replacement electrolytes only, some items containing laxative and replacement electrolytes, and some items containing neither. It should also be understood that a system or kit may comprise more than 10 food items as well.

A semi-solid food may comprise a food with both solid and liquid components mixed together. For example, semi-solid food may comprise a chicken vegetable soup which comprises the solid chicken and vegetables as well as a liquid broth. A semi-solid food that comprises both solid and liquid components mixed together may comprise a percent of solid by weight. For example, a semi-solid food may comprise 10% solid by weight and 90% liquid by weight. For example, in a semi-solid food item weighing 100 grams, if 10% comprises solid food, the solid component weighs 10 grams and the liquid component weighs 90 grams. It should be understood that a semi-solid food may comprise more than 10% solid by weight as well as less than 10% solid by weight. A semi-solid food may comprise, for example, 90% or less liquid by weight. A semi-solid food may comprise, for example, 80% or less liquid by weight. A semi-solid food may comprise, for example, 70% or less liquid by weight. A semi-solid food may comprise, for example, 60% or less liquid by weight. A semi-solid food may comprise, for example, 50% or less liquid by weight. A semi-solid food may comprise, for example, 40% or less liquid by weight. A semi-solid food may comprise, for example, 30% or less liquid by weight. A semi-solid food may comprise, for example, 20% or less liquid by weight. A semi-solid food may comprise, for example, 10% or less liquid by weight.

A semi-solid food may also comprise a food having a relatively high viscosity. A semi-solid food may comprise for example yogurt or pudding.

In an embodiment the system or kit comprises instructions to be provided to a subject. Instructions may comprise written, pictorial, or video instructions and may be provided on numerous different media including a sheet of paper or the screen of a computing device such as a computer, laptop, tablet or smartphone. Instructions may provide the subject with direction as to how to organize the plurality of foods into meals so that, for example, the proper amount of laxative and electrolytes will be ingested by the subject at the proper time. Instructions may similarly direct a subject as to the proper time to eat a particular meal. Instructions may direct a subject to complete the system or kit within a specific period of time, such as, for example, within 24 to 36 hours before a medical or surgical procedure.

In an embodiment, the system or kit also comprises an amount of liquid for a subject to drink. The quantity of liquid may be sufficient to replenish fluid losses and shifts due to the action of the laxative. For example the system or kit may comprise four liters of water that may be divided into smaller servings. Water provided with the system or kit may for example have bicarbonate added so as to make the water's pH basic. The water may, for example, contain electrolytes as well as flavorings. It should be understood that an amount of water greater or less than four liters may also be provided. Likewise, it should be also understood, that the liquid provided may be a juice, tea, coffee, or other flavored drink.

In an embodiment, a food item contains 50% by weight or more of a laxative. In an embodiment, a food item contains 40% by weight or more of a laxative. In an embodiment, a food item contains 30% by weight or more of a laxative. In an embodiment, a food item contains 20% by weight or more of a laxative. In an embodiment, a food item contains 10% by weight or more of a laxative. It should be understood that amounts less than 10% are suitable as well. The laxative may comprise PEG and may further comprise PEG 3350. In an embodiment the amount of PEG 3350 contained in one food item or contained collectively in a plurality of food items comprises 200-300 grams of PEG 3350.

In an embodiment, the plurality of food items provided in the system or kit are the only food items ingested by the subject during a certain period. A subject may be instructed to drink liquid that is not provided in the system or kit in addition to eating only the food items provided in the system or kit.

In an embodiment, the system or kit provides nutrition to the subject as well during the period which the system or kit is used. If, for example, the system or kit is used over a period of 24 to 36 hours then the system or kit may collectively provide a quantity of calories that is sufficient for a subject. The quantity of calories may vary for adults and children and for male and female subjects. The system or kit may also comprise lite versions of the meals and food items which comprise low calorie versions of the meals and food items. The lite versions of the meals and food items will still however provide the same amount of laxative and electrolytes. The collective calorie content of the plurality of food items in the system or kit may comprise between 600-3,000 calories. It should be understood that other calorie quantities are suitable as well including calorie amounts less than 600 calories and more than 3,000 calories.

Food items within the system or kit may comprise, for example, about 20 calories. Food items within the system or kit may comprise, for example, about 40 calories. Food items within the system or kit may comprise, for example, about 80 calories. Food items within the system or kit may comprise, for example, about 100 calories. Food items within the system or kit may comprise, for example, about 150 calories. Food items within the system or kit may comprise, for example, about 200 calories. Food items within the system or kit may comprise, for example, about 250 calories. Food items within the system or kit may comprise, for example, about 300 calories. Food items within the system or kit may comprise, for example, about 350 calories. Food items within the system or kit may comprise, for example, about 400 calories. Food items within the system or kit may comprise, for example, about 450 calories. Food items within the system or kit may comprise, for example, about 500 calories. Food items within the system or kit may comprise, for example, about 550 calories. Food items within the system or kit may comprise, for example, about 600 calories. Food items within the system or kit may comprise, for example, about 650 calories. Food items within the system or kit may comprise, for example, about 700 calories. Food items within the system or kit may comprise, for example, about 750 calories. Food items within the system or kit may comprise, for example, about 800 calories. Food items within the system or kit may comprise, for example, about 850 calories. Food items within the system or kit may comprise, for example, about 900 calories. Food items within the system or kit may comprise, for example, about 100 calories.

Similarly the food items in the system or kit provide other elements of a typical diet. This may comprise protein, fat, minerals and vitamins. The protein, fat, minerals, and vitamins provided by food items are in quantities that are in accordance with a healthy diet and the dietary needs of a particular subject.

In an embodiment, a system or kit will comprise a plurality of food items that are appropriate for individuals with special dietary requirements. Non-limiting examples of special diets include diabetic diets, renal diets, low sodium diets, gluten free diets, low calorie diets, high protein diets, vegetarian diets, vegan diets, kosher diets, and halal diets.

Electrolytes that are lost due to GI losses are replaced per orally in one or more food items. Generally, oral replacement of electrolytes is a less efficient mode of electrolyte replacement relative to intravenous replacement. Because oral replacement of electrolytes is less efficient than intravenous replacement, oral replacement typically requires a far larger quantity of electrolytes provided per orally than intravenously to measurably raise the intravenous levels of electrolytes. Electrolytes contained in one or more food items may comprise salts of electrolytes or the electrolytes may be in solution. When one or more food items in a plurality of food items comprise replacement electrolytes, the quantity of replacement electrolytes present is the collective quantity of replacement electrolytes present in the plurality of food items.

Figure 2:
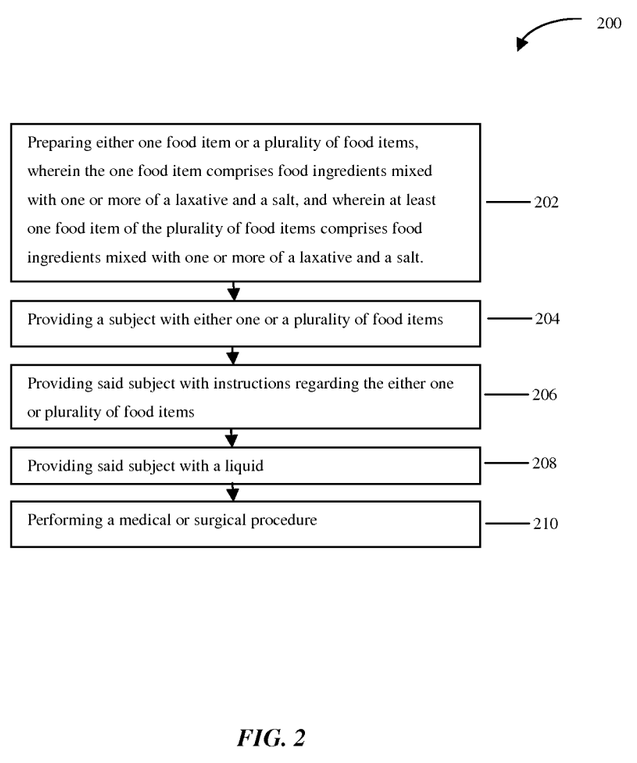
FIG. 2 shows a schematic representation of a method for replacing electrolytes lost by a subject due to ingesting a laxative.

FIG. 2 shows a schematic representation of a method 200 for replacing electrolytes lost by a subject due to ingesting a laxative. In an embodiment the subject has ingested the laxative as a preparation of the subject's digestive tract for a medical or surgical procedure. Non-limiting examples of medical and surgical procedures include colonoscopy and bowel resection.

In a step 202, either one food item or a plurality of food items are prepared, wherein the one food item comprises food ingredients mixed with one or more of a laxative and replacement electrolytes provided, for example, in the form of a salt, and wherein at least one food item of the plurality of food items comprises food ingredients mixed with one or more of a laxative and a salt. The food ingredients and the laxative and replacement electrolytes may be mixed together in a way that ensures homogeneity or near homogeneity of the components. One food item may be provided that comprises food ingredients mixed together with one or more of a laxative such as, for example, PEG 3350, and at least one salt. Quantities of PEG and electrolytes contained within the one food item may comprise, for example, 1-3,000 milligrams of sodium, 1-3,000 milligrams of potassium, 1-750 ml of water, and 5-150 grams of PEG.

A plurality of food items may be provided wherein at least one food item comprises food ingredients mixed together with one or more of a laxative and a salt. Quantities of PEG and electrolytes collectively contained within the plurality of food items may collectively comprise, for example, 3000-11500 milligrams of sodium, 750-4000 milligrams of potassium, 2000-4000 ml of water, and 200-420 grams of PEG.

In a step 204, a subject is provided with one or more food items. The food items may be delivered to the home of the subject. The food items may be sold over the counter at a store or pharmacy. The food items may require a prescription to purchase. The food items may be provided by a physician in his or her office.

In a step 206, the subject may be provided with instructions. Instructions may comprise written, pictorial, or video instructions and may be provided on numerous different media including a sheet of paper or the screen of a computing device such as a computer, laptop, tablet or smartphone. Instructions may provide the subject with direction as to how to organize the plurality of foods into meals so that, for example, the proper amount of laxative and electrolytes will be ingested by the subject at the proper time. Instructions may similarly direct a subject as to the proper time to eat a particular meal. Instructions may direct a subject to complete the system or kit within a specific period of time, such as, for example, within 24 to 36 hours before a medical or surgical procedure.

In a step 208, the subject may be provided with a liquid to drink. The quantity of liquid may be sufficient to replenish fluid losses and shifts due to the action of the laxative. For example the system or kit may comprise four liters of water that may be divided into smaller servings. Water provided with the system or kit may for example have bicarbonate added so as to make the water's pH basic. The water may, for example, contain electrolytes as well as flavorings. It should be understood that an amount of water greater or less than four liters may also be provided. Likewise, it should be also understood, that the liquid provided may be a juice, tea, coffee, or other flavored drink.

In a step 210, the subject may have a medical or surgical procedure performed.

The food bars described herein may be consumed or provided for consumption, for example, by a subject preceding a procedure that requires a clean bowel, i.e., a medical procedure such as a surgical or diagnostic procedure, to prepare the bowel for the procedure. Such procedures include colonoscopy, intestinal surgery, virtual colography, fiberoptic endoscopy, sigmoidoscopy, wireless capsule endoscopy (WCE) (which uses a miniaturized scope administered in a "pill" form) and barium studies (barium enema), inter alia.

In some embodiments, the ingestion of these food bars can start at 72, 48, 36, 24, or 12 hours prior to a scheduled procedure; these food bars can be consumed up to a few hours prior to the procedure, for example, up to about 2, 3, 4, 5, or 6 hours prior to the procedure. In general, these methods of preparing the bowel do not include the use of a high-volume liquid prep as is known in the art (described above) for whole bowel irrigation. An enema, for example, a tap water enema, may be used in some cases. As noted above, food bars for use in preparing the subject for a procedure will preferably be prepared from low fiber, low residue ingredients. In these embodiments, the subject is provided with and consumes a number of the bars sufficient to induce the presence of watery yellow stools with light yellow or clear effluent within about 6-8 hours of the initiation of the prep; this effluent is a clinical indicator of an adequate cleansing of the colon and is used as a clinical guide and surrogate marker for an adequate colon cleansing to permit a thorough inspection of the lining of the colon. In some embodiments, the number of bars provided for consumption is sufficient to provide 200-400 grams of PEG per menu.

While preferred embodiments of the presently described subject matter have been shown and described herein, it will be obvious to those skilled in the art that such embodiments are provided by way of example only. Numerous variations, changes, and substitutions will now occur to those skilled in the art without departing from the described subject matter. It should be understood that various alternatives to the embodiments of the subject matter described herein may be employed in practicing the described subject matter. It is intended that the following claims define the scope of the described subject matter and that methods and structures within the scope of these claims and their equivalents be covered thereby.

Further details are illustrated by the following non-limiting Examples section.

EXAMPLES

Example 1: Lemon Cooler Bar

Lemon cooler bar is an example of a food bar that contains either more than 50% of PEG by weight or less than 50% PEG by weight. Table V lists exemplary ingredients of a lemon cooler bar and the percentage and quantity of the exemplary ingredients.

TABLE V

| Ingredient | Percentage | Quantity per 1000 Grams |
| --- | --- | --- |
| PEG | 55.07% | 550.73 |
| Rice Syrup | 30.82% | 308.21 |
| Sugar | 6.41% | 64.13 |
| Coconut Oil | 2.94% | 29.37 |
| Glycerin | 1.47% | 14.69 |
| Citric acid | 0.12% | 1.17 |
| Total | 100.00% | 1000.00 grams |

Additional ingredients included lemon yogurt coating, vanilla flavor, and lemon flavor. The lemon cooler bars were produced without excessive heating of PEG, for example PEG-3350. To produce the lemon cooler bars, PEG, for example, PEG-3350, was first mixed with the dry ingredients such as sugar, vanilla, and lemon flavor powders. The mixture of the dry ingredients was blended with melted coconut oil and glycerin at room temperature, for example, a temperature below 80° F. (26.7° C.), to form a fondant-like mass. The fondant-like mass was blended with rice syrup and mixed sufficiently to ensure a homogeneous dispersion of the ingredients. The mixture was then shaped into bars of about 70 grams. About 1.5 gram of melted lemon burst yogurt coating was added in a drizzle pattern on each bar. When dissolving in the mouth, PEG produces a cooling effect, which can be utilized in choosing the flavor for the bar, such as the refreshing lemon flavor.

Table VI shows the nutritional breakdown of an exemplary lemon cooler bar.

TABLE VI

| Item | Quantity |
| --- | --- |
| PEG | 38.6 g |
| Na | 20.7 mg |
| K | 9.22 mg |
| Fiber | 0.08 g |
| Fat | 2.52 g |
| Calorie | 119.39 |
| Total | 71.5 grams |

Table VII shows a nutritional breakdown of a second embodiment of a lemon cooler bar.

TABLE VII

| Item | Quantity |
| --- | --- |
| PEG | 35.44 g |
| Na | 18.63 mg |
| K | 8.30 mg |
| Fiber | 0.07 g |
| Fat | 2.27 g |
| Calorie | 107.45 |
| Total | 64.35 g |

Example 2: Salted Caramel Crisp Bar

Salted caramel crisp bar is another example of a food bar that contains either more than 50% of PEG by weight or less than 50% PEG by weight. Table VIII lists exemplary ingredients of a salted caramel crisp bar and the percentage and quantity of the exemplary ingredients.

TABLE VIII

| Ingredient | Percentage | Quantity per 1000 Grams |
| --- | --- | --- |
| PEG | 50.00% | 500 |
| Rice Syrup | 32.00% | 320 |
| Coconut Oil | 2.00% | 20 |
| Glycerin | 2.00% | 20 |
| Total | 100.00% | 1000.00 grams |

Additional ingredients include sea salt, rice crisps and caramel flavor.

The salted caramel crisp bars were produced without excessive heating of PEG-3350. To produce the salted caramel crisp bars PEG-3350, was first mixed with the dry ingredients such as sea salt and caramel flavor powders. The mixture of the dry ingredients was blended with melted coconut oil and glycerin at room temperature, for example, a temperature below 80° F. (26.7° C.), to form a fondant-like mass. The fondant-like mass was then blended with rice syrup and mixed sufficiently to ensure a homogeneous dispersion of the ingredients. Rice crisps were gently folded in the mixture. The mixture was shaped into bars of about 70 grams. When dissolving in the mouth, PEG produces a cooling effect, which can be disguised by the caramel flavor of the bar. Rice crisps were added to give an alternative texture and may improve taste and boost compliance.

Table IX shows the nutritional breakdown of an exemplary salted caramel crisp bar.

TABLE IX

| Item | Quantity |
| --- | --- |
| PEG | 35 g |
| Na | 156 mg |
| K | 9.51 mg |
| Fiber | 0.228 g |
| Fat | 1.63 g |
| Calories | 125.26 |
| Total | 70 grams |

Table X shows a nutritional breakdown of a second embodiment of a salted caramel crisp bar.

TABLE X

| Item | Quantity |
| --- | --- |
| PEG | 31.50 g |
| Na | 140.40 mg |
| K | 8.56 mg |
| Fiber | 0.21 g |
| Fat | 1.47 g |
| Calories | 112.73 |
| Total | 63 grams |

Example 3: Savory Humus Bar

A savory humus bar is produced in accordance with the methods described herein. Table XI shows a nutritional breakdown of an exemplary savory humus bar.

TABLE XI

| Item | Quantity |
| --- | --- |
| PEG | 23.31 g |
| Na | 341.91 mg |
| K | 10.85 mg |
| Fiber | 1.29 g |
| Fat | 7.17 g |
| Calories | 158.48 |
| Total | 63 grams |

Example 4: Vanilla Shake

A vanilla shake is produced in accordance with the methods described herein. Table XII shows a nutritional breakdown of an exemplary vanilla milkshake.

TABLE XII

| Item | Quantity |
| --- | --- |
| PEG | 114.38 g |
| Na | 101.91 mg |

TABLE XII-continued

| Item | Quantity |
| --- | --- |
| K | 289.19 mg |
| Fiber | 0.00 g |
| Fat | 0.13 g |
| Calories | 134.52 |
| Total | 339.29 g/11 fl. oz. |

Example 5: Ginger Candy

A ginger candy is produced in accordance with the methods described herein. Table XIII shows a nutritional breakdown of an exemplary ginger candy.

TABLE XIII

| Item | Quantity |
| --- | --- |
| PEG | 0 g |
| Na | 5 mg |
| K | 0 mg |
| Fiber | 0.1 g |
| Fat | 0.1 g |
| Calories | 15.4 |
| Total | 4 g |

Example 6: Banana Strawberry Refresher

A banana strawberry refresher is produced in accordance with the methods described herein. Table XIV shows a nutritional breakdown of an exemplary banana strawberry refresher.

TABLE XIV

| Item | Quantity |
| --- | --- |
| PEG | 116.63 g |
| Na | 12.61 mg |
| K | 3.58 mg |
| Fiber | 0.28 g |
| Fat | 0.00 g |
| Calories | 72.08 |
| Total | 339.29 g/11 fl oz |

Example 7: Chicken and Rice

Chicken and rice is produced in accordance with the methods described herein. Table XV shows a nutritional breakdown of exemplary chicken and rice.

TABLE XV

| Item | Quantity |
| --- | --- |
| PEG | 0 g |
| Na | 2130 mg |
| K | 250 mg |
| Fiber | 1 g |
| Fat | 1 g |
| Calories | 230 |
| Total | 8.5 oz |

Example 9: Crackers

Crackers are produced in accordance with the methods described herein. Table XVI shows a nutritional breakdown of exemplary crackers.

TABLE XVI

| Item | Quantity |
| --- | --- |
| PEG | 0 g |
| Na | 33.75 mg |
| K | 0 mg |
| Fiber | 0.27 g |
| Fat | 0.54 g |
| Calories | 45 |
| Total | 6 each |

Example 12: Ziti Minestrone

Ziti Minestrone is produced in accordance with the methods described herein. Table XVII shows a nutritional breakdown of exemplary ziti minestrone.

TABLE XVII

| Item | Quantity |
| --- | --- |
| PEG | 0 g |
| Na | 2830 mg |
| K | 150 mg |
| Fiber | 2 g |
| Fat | 1 g |
| Calories | 160 |
| Total | 13 oz. |

Example 13: Garlic Crackers

Garlic crackers are produced in accordance with the methods described herein. Table XVIII shows a nutritional breakdown of exemplary garlic crackers.

TABLE XVIII

| Item | Quantity |
| --- | --- |
| PEG | 0 g |
| Na | 120 mg |
| K | 0 mg |
| Fiber | 0.7 g |
| Fat | 1.1 g |
| Calories | 45 |
| Total | 3 each |

Example 14: A System

One or more of the food items above may be provided to a patient prior to a medical or surgical procedure. Table XIX shows an exemplary system comprising multiple food items as described herein and in the above examples. Also shown is an exemplary schedule for the patient to consume the food items in order to deliver the laxative and replacement electrolytes to fully purge the GI tract of the patient while effectively replacing electrolytes by the action of the laxative.

TABLE XIX

| LUNCH - Noon | SNACK - 3 pm | DINNER - 6 pm | SNACK - 8 pm | MORNING - 4.5 hr prior to procedure |
| --- | --- | --- | --- | --- |
| Chicken & Rice | Lemon Cooler Bar | Ziti Minestone | Vanilla Milkshake | Banana Strawberry Refresher |

TABLE XIX-continued

| LUNCH - Noon | SNACK - 3 pm | DINNER - 6 pm | SNACK - 8 pm | MORNING - 4.5 hr prior to procedure |
|---|---|---|---|---|
| Water | Electrolyte Supplement (optional) | Garlic Crackers | Salted Caramel Crisp Bar | |
| Crackers | | Water | Electrolyte Supplement (optional) | |
| | | | Ginger Candy | |

What is claimed is:

1. A composition comprising:
   50% to 80% by weight of a polyethylene glycol;
   a food ingredient; and
   a hydrophobic binder;
   wherein the food ingredient and the hydrophobic binder together make up 10% to 50% by weight of the composition;
   wherein the composition comprises a solid that is a mixture of the polyethylene glycol, the food ingredient, and the binder;
   wherein the composition is substantially free of a thermal degradation product of the polyethylene glycol formed at a temperature of 80 to 100 degrees Fahrenheit; and
   wherein the hydrophobic binder is selected from the group consisting of coconut oil, lard, vegetable shortening, palm oil, cocoa butter, butter, or margarine.

2. The composition of claim 1, wherein the binder binds the laxative and the food ingredients together thereby forming the solid.

3. The composition of claim 1, wherein the binder makes up 1% to 3% of a total weight of the composition.

4. The composition of claim 1, wherein the composition comprises electrolytes comprising one or more of sodium chloride, potassium chloride, potassium bicarbonate, or magnesium chloride.

5. The composition of claim 1, wherein the mixture comprises a homogenous mixture.

6. The composition of claim 1, wherein the composition is a fondant.

7. The composition of claim 1, wherein the composition is a bar.

8. The composition of claim 1, wherein the composition is shelf-stable for up to one year.

9. A method for producing a bowel movement in an individual, comprising:
   melting a hydrophobic binder;
   mixing a food ingredient together with a polyethylene glycol at 80 to 100 degrees Fahrenheit or less, and further mixing the food ingredient and the polyethylene glycol together with the hydrophobic binder that is melted thus creating a semi-solid mixture;
   forming a solid food item from the semi-solid mixture at 80 to 100 degrees Fahrenheit or less wherein the solid food item comprises 50% to 80% by weight of the polyethylene glycol;
   providing to said individual the solid food item in order to produce said bowel movement in said individual;
   wherein the food ingredient and the hydrophobic binder together make up 10% to 50% by weight of the composition; and
   wherein the hydrophobic binder is selected from the group consisting of coconut oil, lard, vegetable shortening, palm oil, cocoa butter, butter, or margarine.

10. The method of claim 9, wherein the binder is cocoa butter.

11. The method of claim 9, wherein the binder makes up 1% to 3% of a total weight of the composition.

12. The method of claim 9, wherein the solid food item comprises electrolytes comprising one or more of sodium chloride, potassium chloride, potassium bicarbonate, or magnesium chloride.

13. The method of claim 9, wherein the semi-solid mixture comprises a homogenous mixture.

14. The method of claim 9, wherein the solid food item does not substantially contain laxative breakdown products.

15. The method of claim 9, wherein the semi-solid mixture comprises a fondant.

16. The method of claim 9, wherein the solid food item is shelf-stable for up to one year.

17. The method of claim 9, wherein forming the solid food item comprises extruding the semi-solid mixture together with a syrup to form a solid food item sheet.

18. The composition of claim 1, wherein the laxative comprises PEG 3350.

19. The composition of claim 1, wherein the binder makes up 1% to 30% by weight of the composition.

20. The composition of claim 1, wherein the composition is shelf-stable for up to two years.

21. The composition of claim 1, wherein the composition comprises a flavoring substance comprising a natural flavoring substance, a nature-identical flavoring substance, an artificial flavoring substance or a combination thereof.

22. The composition of claim 21, wherein the flavoring substance comprises at least one of a lemon flavorant, a mint flavorant, a ginger flavorant, a pepper flavorant, a vanilla flavorant, a caramel flavorant or a chocolate comprising white chocolate, dark chocolate, milk chocolate, semi-sweet chocolate, sweet chocolate, hard chocolate, soft chocolate, bitter chocolate, Cocoa mass, cocoa butter mix, and hard boiled toffees.

23. The composition of claim 22 wherein the flavoring substance comprises at least one of a lemon flavorant, a mint flavorant, a vanilla flavorant, a caramel flavorant or a chocolate flavorant.

24. The composition of claim 1 wherein the composition comprises a sweetener.

25. The composition of claim 6, wherein the fondant is extruded to form a bar.

* * * * *